(12) United States Patent
Xia et al.

(10) Patent No.: US 8,467,977 B2
(45) Date of Patent: Jun. 18, 2013

(54) FIBER OPTIC CARBON DIOXIDE PURITY SENSOR PACKAGE AND SYSTEM

(75) Inventors: Hua Xia, Altamont, NY (US); Anthony James George, Clifton Park, NY (US); Renato Guida, Wynantskill, NY (US); James Daniel Antalek, Valatie, NY (US); James Thomas Clark, Clifton Park, NY (US); Jeffrey James Andritz, Altamont, NY (US); Michael James Palleschi, Clifton Park, NY (US); Dennis Anthony Pasquarella, Schenectady, NY (US); Aniceto Domingo Bantug, IV, Clifton Park, NY (US)

(73) Assignee: General Electric Company, Niskayuna, NY (US)

( * ) Notice: Subject to any disclaimer, the term of this patent is extended or adjusted under 35 U.S.C. 154(b) by 302 days.

(21) Appl. No.: 12/845,871

(22) Filed: Jul. 29, 2010

(65) Prior Publication Data
US 2012/0029835 A1 Feb. 2, 2012

(51) Int. Cl.
*G02B 6/34* (2006.01)
(52) U.S. Cl.
USPC ............................................ 702/24; 702/22
(58) Field of Classification Search
USPC .................. 702/22, 24; 385/12–14, 37, 147
See application file for complete search history.

(56) References Cited

U.S. PATENT DOCUMENTS

| | | | |
|---|---|---|---|
| 5,714,121 A | 2/1998 | Alderete et al. | |
| 6,989,246 B2 | 1/2006 | Yeh | |
| 7,151,872 B1 | 12/2006 | Xia et al. | |
| 7,489,835 B1 | 2/2009 | Xia et al. | |
| 2006/0215959 A1* | 9/2006 | McCarthy et al. | 385/37 |
| 2007/0048181 A1 | 3/2007 | Chang et al. | |
| 2010/0070198 A1 | 3/2010 | Speranza et al. | |

FOREIGN PATENT DOCUMENTS

| | | |
|---|---|---|
| DE | 19900019 A1 | 8/2000 |
| EP | 2202548 A1 | 6/2010 |
| GB | 2478829 A | 9/2011 |
| WO | 03071235 A1 | 8/2003 |
| WO | 2008136870 A2 | 11/2008 |

OTHER PUBLICATIONS

Search Report from corresponding GB Application No. GB1112281.9 dated Jun. 29, 2012.

* cited by examiner

*Primary Examiner* — Sujoy Kundu
(74) *Attorney, Agent, or Firm* — Ann M. Agosti

(57) ABSTRACT

A carbon dioxide ($CO_2$) purity sensor package includes a fiber core, a periodic refractive index modulated fiber grating structure within the fiber core and a fiber cladding. A thermally conductive sensing layer is positioned about a portion of the fiber cladding surrounding the periodic refractive index modulated fiber grating structure. A gas chamber encloses the fiber cladding with the thermally conductive sensing layer.

15 Claims, 8 Drawing Sheets

FIBER OPTIC CARBON DIOXIDE PURITY SENSOR PACKAGE AND SYSTEM

BACKGROUND

The invention relates generally to carbon dioxide purity detection and more specifically to fiber optic carbon dioxide purity sensors and packages.

The detection and measurement of various combustible and toxic gases are important functions in a wide variety of industries. For example, carbon dioxide (CO2) purity detection and measurement are often desired or required functions in fields such as demand-control ventilation, transportation, carbon capture, the food processing, oil refinery and chemical industries, and industrial system maintenance.

CO2 purity detection has been investigated for many years, and many kinds of sensing embodiments based on electrical, optical, and electrochemical sensors have been introduced into the marketplace. Existing CO2 purity monitoring instruments are typically based on thermal conductivity detection (TCD) or Nondispersive Infrared (NDIR) optical detection methods. TCD is a general-purpose gas analysis method with non-specific and nondestructive characteristics but does not provide high resolution for accurate CO2 gas purity analysis because of thermal drifting issues. Similarly, NDIR optical detection has limitations in measuring purity of CO2 when CO2 is blended with other hydrocarbon gases. Other methods for monitoring CO2 purity include the use of gas density and differential pressure based measurements. Fluorescence detection based on dye embedded polymeric thin film material integrated with a bared fiber tip is another optical method for monitoring CO2 gas purity in a fluid medium. However, these methods are subject to variations in light absorption due to variations in temperature, pressure, and density of the CO2 gas, and thereby result in baseline drift and accuracy degradation.

Therefore, there is a need for an improved carbon dioxide purity measurement sensor and system to address one or more of the aforementioned issues.

BRIEF DESCRIPTION

In accordance with an embodiment of the present invention, a carbon dioxide (CO2) purity sensor package including a fiber core, a fiber cladding, and a periodic refractive index modulated fiber grating structure within the fiber core is provided. The sensor package further includes a thermally conductive sensing layer positioned about a portion of the fiber cladding surrounding the periodic refractive index modulated fiber grating structure and a gas chamber enclosing the fiber cladding with the nano structural thermally conductive sensing layer.

In accordance with another embodiment of the present invention, a system for measuring carbon dioxide (CO2) purity including a light source for providing an optical signal through a fiber optic cable and a CO2 purity sensor for receiving the optical signal is provided. The CO2 purity sensor includes a periodic refractive index modulated fiber grating structure with a thermally conductive sensing layer integrated with a fiber cladding structure. The system further includes a thermally insulated cylindrical gas chamber for maintaining the CO2 purity sensor in an isothermal state, a photodetector for receiving a reflected optical signal from the CO2 purity sensor and a processing circuitry coupled to the photodetector for analyzing the reflected optical signal.

In accordance with yet another embodiment of the present invention, a system for measuring multi-point carbon dioxide (CO2) purity is provided. The system includes a light source for providing an optical signal through an optical splitter to a plurality of CO2 sensor packages, a photodetector array for receiving reflected optical signals from the plurality of CO2 purity sensor packages and a processing circuitry coupled to the photodetector array for analyzing the reflected optical signals. The CO2 purity sensor package includes a periodic refractive index modulated fiber Bragg grating structure within a fiber core and a thermally conductive sensing layer integrated with a fiber cladding structure. The CO2 purity sensor package further includes an apodized fiber Bragg grating within the fiber core for sensing a baseline temperature and variations in the baseline temperature and a thermally insulated cylindrical gas chamber for maintaining the CO2 purity sensor package in an isothermal state.

DRAWINGS

These and other features, aspects, and advantages of the present invention will become better understood when the following detailed description is read with reference to the accompanying drawings in which like characters represent like parts throughout the drawings, wherein.

DETAILED DESCRIPTION

When introducing elements of various embodiments of the present invention, the articles "a," "an," "the," and "said" are intended to mean that there are one or more of the elements. The terms "comprising," "including," and "having" are intended to be inclusive and mean that there may be additional elements other than the listed elements.

Figure 1:
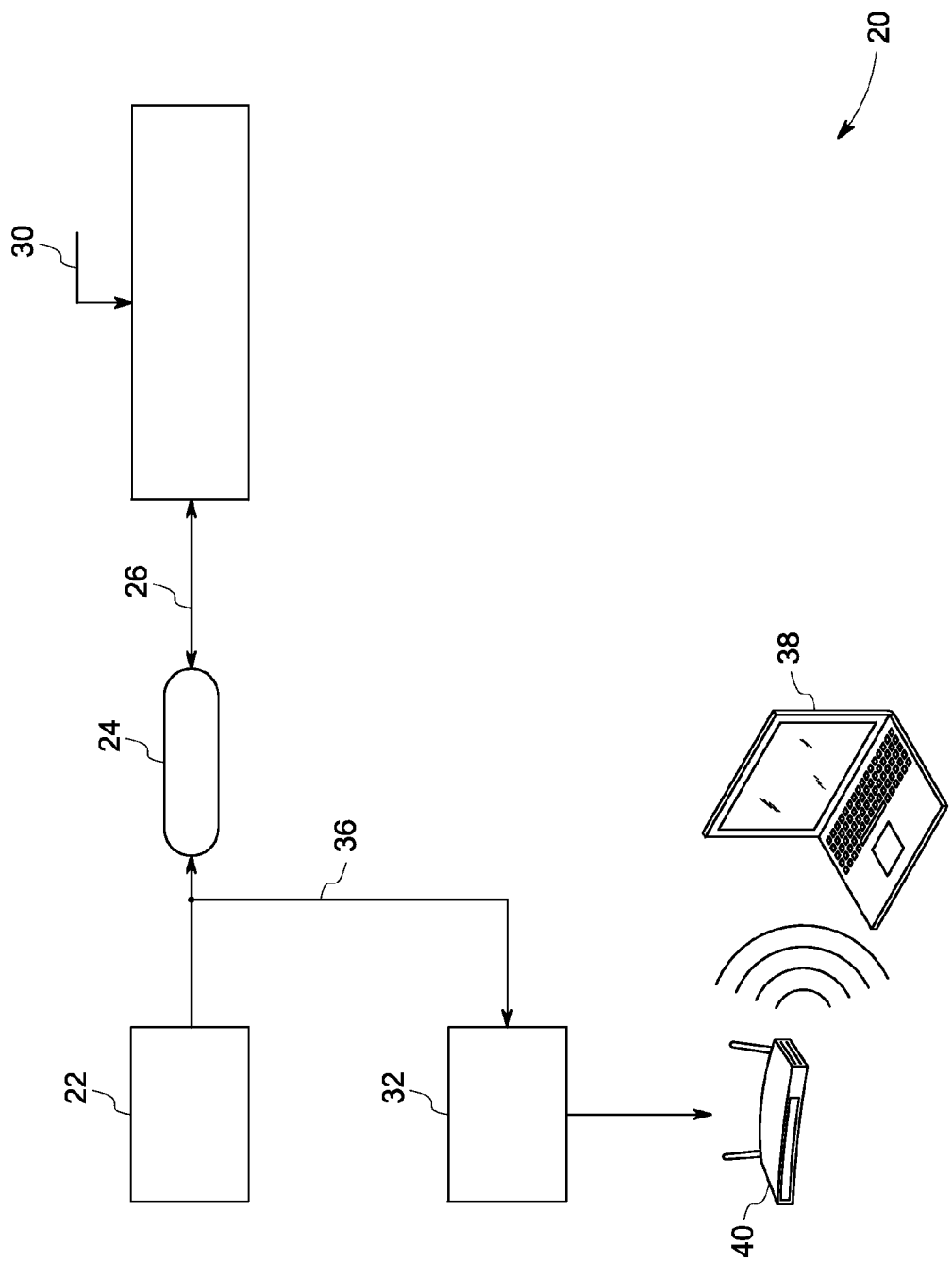
FIG. 1 is a schematic view of a carbon dioxide (CO2) gas purity sensing system including a fiber CO2 gas purity sensor package in accordance with an embodiment of the present invention.

FIG. 1 is a schematic illustration of a carbon dioxide (CO2) gas purity sensing system 20 including a fiber CO2 gas purity sensor package according to an embodiment of the invention. In general, sensing system 20 includes a light source 22, such as tunable, broadband light source, in light communication with an optical coupler or circulator 24. Optical coupler 24 receives the light transmitted from light source 22 and transmits a portion of the light through an optical fiber cable 26. The light passing through optical fiber cable 26 enters a fiber gas sensor or a fiber CO2 gas purity sensor 30. A portion of the light reflected by fiber gas sensor 30 is received by photodetector 32 through an optical fiber cable 36. The converted light signal generated by photodetector 32 is transmitted to a processing circuitry or a data acquisition unit 38. In one embodiment, a wireless interface 40 transmits electrical signals to data acquisition unit 38, and data acquisition unit 38 uses the reflected signals to monitor the purity of the CO2 gas. In another embodiment, an Ethernet cable is used to transmit electrical signals to data acquisition unit 38, and data acquisition unit 38 uses the transmitted signals to analyze the CO2 purity from a sampling source or targeted environment.

Figure 2:
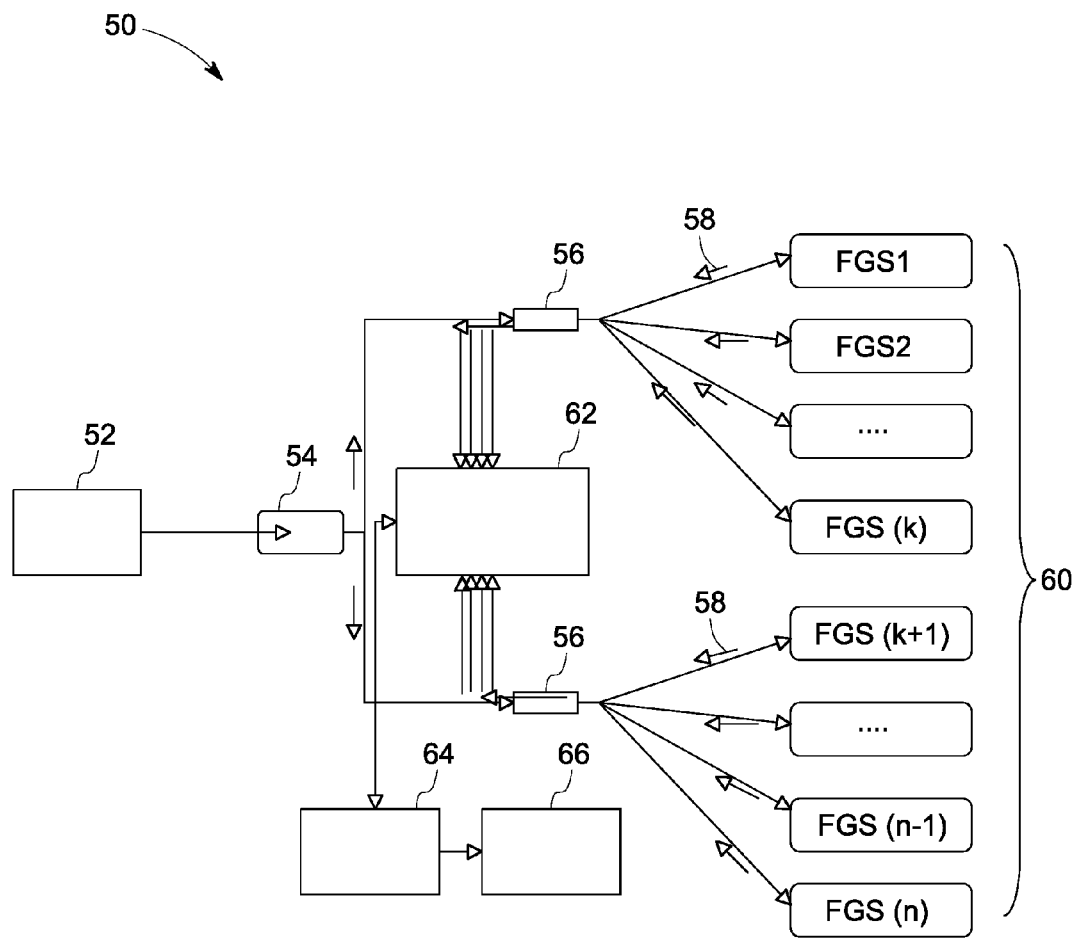
FIG. 2 is a schematic view of a carbon dioxide (CO2) gas purity sensing system including multiple fiber CO2 gas purity sensor packages in accordance with an embodiment of the present invention.

FIG. 2 is a schematic illustration of a carbon dioxide (CO2) gas purity sensing system 50 including multiple fiber CO2 gas purity sensor packages according to an embodiment of the invention. In general, sensing system 50 includes a light source 52, such as tunable, broadband light source, in light communication with a 1×2 optical splitter 54. Optical splitter 54 transmits a light signal to a 1×N optical splitter 56 which then passes the light through a plurality of optical fiber cables 58 and enters an array of fiber gas sensors (FGS) 60. Light signals reflected by fiber gas sensors 60 are received by a photodetector array 62. In one embodiment, a wavelength-multiplexing method is used. Light signals from photodetector array 62 are then transmitted to a processing circuitry or a data acquisition unit 66 to monitor the purity of the CO2 gas. In one embodiment, a wireless interface 64 transmits electrical signals to data acquisition unit 66. In one embodiment, a fiber CO2 gas purity sensor package is installed inside an apparatus for CO2 purity detection. A plurality of fiber CO2 gas purity sensors may be installed at multiple locations for simultaneous multi-point CO2 purity detection.

Figure 3:
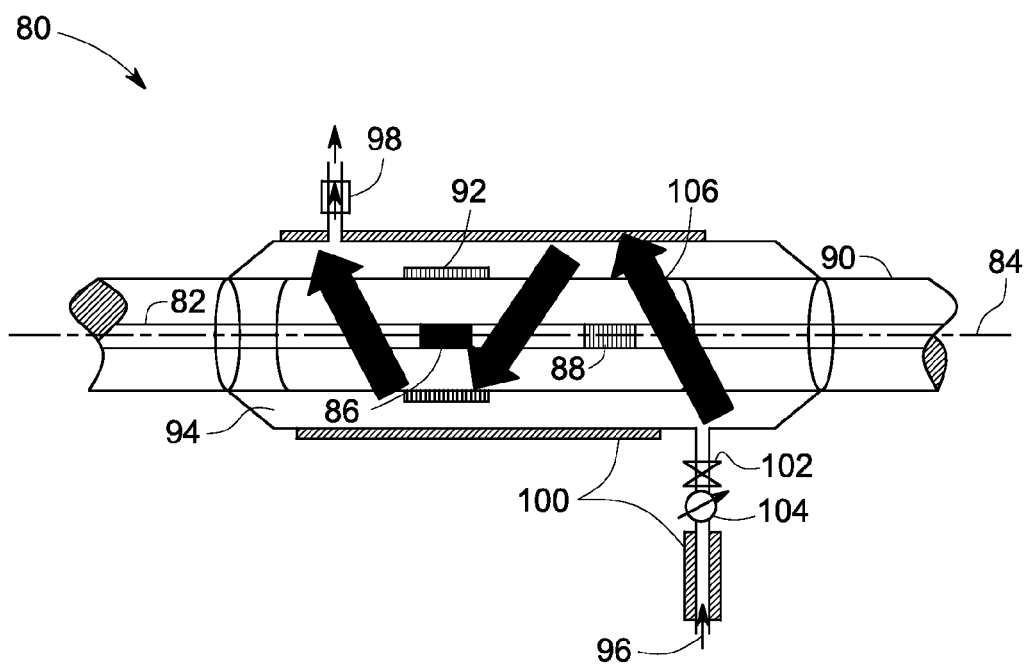
FIG. 3 is a schematic representation of a fiber CO2 gas purity sensor package in accordance with an embodiment of the present invention.

FIG. 3 shows a fiber CO2 gas purity sensor package 80 in accordance with an embodiment of the present invention. Sensor package 80 includes fiber gratings 86, 88, thermal stabilizers 100, a gas chamber 94, and a central fiber core 82 that extends along a longitudinal axis 84. In one embodiment, central fiber core 82 comprises germanium dioxide (GeO2) or fluorine (F) co-doped silica and has a diameter ranging from about 5 microns to about 9 microns. Fiber core 82 may include two refractive index periodic modulated gratings 86, 88 having different amplitude modulation profiles. In one embodiment, the periodic modulated grating may comprise an apodized, blazed, or blazed and apodized modulation, for example, for increasing guided core mode coupling to cladding modes by shedding guided mode field energy to a fiber cladding 90. In one embodiment the grating length ranges from 3 millimeters to 25 millimeters and the grating type comprises a Bragg grating.

In one embodiment, a sensing layer 92 is formed around fiber cladding 90 in the region of modulated fiber grating 86, and grating 88 comprises an apodized fiber grating structure 88 within fiber core 82 at a distance along longitudinal axis 84 with respect to fiber grating structure 86. Fiber grating structure 88 may be used for determining the baseline temperature of the sensor and also variations in the baseline temperature due to an inlet gas temperature variation in real time; and thereby may used to correct gas sensor baseline variation.

Fiber cladding 90 is circumferentially disposed about fiber core 82 and, in one embodiment, includes pure silica or fluorine doped silica with an outer diameter of about 125 microns. In one embodiment, fiber cladding 90 is configured to act as a waveguide for light propagation through fiber core 82. A broadband tunable light source 22 (FIG. 1) or 52 (FIG. 2) is positioned in light communication with the optical fiber cable and emits a near infrared light that propagates through fiber core 82.

Fiber grating structure 86 is surrounded by a thermally conductive sensing layer 92 that in one embodiment comprises a nanostructural thin film. In one embodiment, thermally conductive sensing layer 92 comprises a metallic thin film 92 disposed on fiber Bragg grating cladding 90 by a magnetron sputtering film growth process. In one embodiment of the magnetron sputtering film growth process, the substrate temperature or the fiber Bragg grating temperature is close to ambient, and a $3.0\times10^{-3}$ Torr vacuum chamber is used. Thermally conductive sensing layer 92 includes in one embodiment a sandwiched triple layer structure wherein the first layer comprises a titanium or chrome based bonding material of 30-50 nanometer thickness, the middle layer includes thermally conductive material (Cu, Au, Al etc) of 100-400 nanometers thickness, and the top layer includes Ni, Ti, Au, or combinations thereof as a capping layer of 30-50 nanometers thickness for protecting the sensing material from oxidization, corrosion, and erosion. In one embodiment, the thickness of sensing layer 92 ranges from 50 nanometers to 500 nanometers. In some embodiments, thermally conductive non-metallic films may be used as the sensing layer.

Gas chamber 94 includes a gas inlet 96 and a gas outlet 98 and is used for maintaining fiber sensor interaction with an input gas stream. Gas chamber 94 may be hermetically sealed and protected with a fiberglass based thermal insulation material and maintains fiber grating structure 86 in a thermally high energized state or, in other words, increases the temperature of fiber grating structure 86. For example, if the potential maximum input gas temperature is 100 deg C., then the fiber grating structure temperature is increased to a temperature higher than that 100 deg C. In one embodiment, the fiber grating structure temperature is kept at least 20 deg. C. higher than the input gas temperature. The CO2 gas enters gas chamber 94 through gas inlet 96, interacts with sensing layer 92 and fiber grating structure 86, and exits gas chamber 94 via gas outlet 98. In one embodiment, where the inlet and outlet are selected so as to not provide a direct gas path therebetween, the path through chamber 94 is a zigzag gas flow path 106. A thermal energy transfer between the CO2 gas and sensor 80 results in a wavelength shift of the light signal passing through fiber core 82. Since the thermal energy transfer is dependent upon the nature of the CO2 gas thermal capacity and specific heat, the wavelength shift can be correlated to the measured CO2 gas concentration or CO2 purity in the blended gas. It should also be noted that the fiber CO2 gas sensor response speed depends upon the thermal conductivity property of sensing layer 92.

In one embodiment, a three-way switch valve (not shown) may be provided at gas inlet 96 for circulating a reference gas inside gas chamber 94 before the testing gas or the blended CO2 gas is injected into gas chamber 94 for differentiating CO2 purity sensitivity with zigzag gas flow path 106. A thermal stabilizer 100 may be disposed onto gas chamber 94 and gas inlet 96 for stabilizing temperature. In other words, thermal stabilizer 100 is provided to shield the sensor from ambient temperature variation and keep the sensor package in an isothermal status. The thermal stabilizer maintains gas sensor package thermal fluctuation less than 0.1° C. in one embodiment. The thermal stabilizer may include a heating tape, or a heating pad, or a heating wire that can be combined with a temperature controller (not shown) and thermocouple (not shown) for maintaining the gas chamber at constant temperature. Further, a valve 102 may be provided to control flow of the gas and a flow meter 104 may be provided to measure the amount of the gas flow.

Fiber grating structure 86 is functionalized as a thermal sensitive sensor for measuring CO2 gas concentration and composition because of CO2 gas' small ratio of the specific heat (1.294), low specific heat capacity (0.84 KJ/Kg·K), and high heat of fusion (196.1 kJ/kg) and latent heat of vaporization (571 KJ/Kg) properties. Table 1 shows some physical and chemical properties of several gases. It can be seen from Table 1 that the CO2 gas has higher molecular weight than the rest of the gases. In addition, its latent heat of vaporization is also high but its thermal conductivity is relatively small. Thus, when CO2 gas interacts with the fiber grating structure, the sensing layer integrated fiber grating structure will lose thermal energy to the CO2 gas stream. Thus, its wavelength shift will be modulated by the gas steam. When the thermal energy or the heat energy is withdrawn or transferred from fiber grating structure 86 to the CO2 gas, the thermal energy of the fiber grating or temperature falls, whereas when the heat energy is added around fiber grating structure 86, the thermal energy of the fiber grating or temperature rises. Thus, if fiber CO2 gas sensor 80 is maintained at a stable operating condition, then any temperature variation will modulate wavelength shifts in fiber grating structure 86. In one embodiment, thermal energy variation occurs because of gas flow over fiber grating structure 86 and the thermal energy exchange therebetween.

The resonant wavelength $\lambda_B$ ($T_0$) of fiber grating structure 86 at an ambient temperature $T_0$ is given by:

$$\lambda_B(T_0) = 2 \cdot n \cdot \Lambda(T_0) \quad (1)$$

where n represents an effective refractive index of the fiber core, and $\Lambda$ is the fiber grating structure modulation periodicity.

Further, wavelength response $\Delta\lambda(T)$ of the fiber grating structure 86 at a temperature T can be given by:

$$\Delta\lambda(T) = k_T \cdot (T-T_0) + k_e \cdot \Delta H \quad (2)$$

where $k_T$ is the fiber grating temperature response coefficient given as $k_T \approx (11\pm2)$ pm/° C., and $\Delta H$ is the enthalpy or total heat energy exchange with fiber grating with a calibration factor of $k_e$. In general, the thermal energy exchange is proportional to changes in gas stream temperature and is given by $$\Delta H \propto (T-T_o) \quad (3)$$

With the addition of sensing layer 92, the wavelength response of a fiber grating structure 86 can be given by:

$$\Delta\lambda(T) = \kappa \cdot (T-T_0) \quad (4)$$

where κ represents modified fiber CO2 gas purity sensor temperature response sensitivity.

Sensing layer 92 comprises a thermally conductive material which acts as an effective heat transfer medium and is used to increase fiber Bragg grating sensitivity to surrounding temperature variation induced by the CO2 gas thermal exchange process. The material for sensing layer 92 is selected based on its thermal properties and also the way it interacts with a particular blended gas. Generally, the gas sensor requires a fast response time. Thus, a material that responds to a CO2 gas in few seconds is useful for the sensing layer. In one embodiment, in order to have a good measurable response from fiber CO2 gas purity sensor 80, sensing layer 92 comprises a material with high thermal conductivity and high mass density in a constant temperature environment. The high thermal conductivity sensing layer provides a fast thermal energy exchange from the fiber Bragg grating to the gas stream. In one embodiment, the thermal conductivity of the conductive sensing layer may range from about 71 W/m·K to about 429 W/m·K. Examples of thin sensing layer material include aluminum, copper, nickel, cobalt, silver, gold, palladium, and platinum. The examples further include diamond, diamond-like carbon (DLC), Indium tin oxides (ITO) with controlled porous structure or nanoparticle morphology. With a typical thickness from several tens of nanometers to several hundreds of nanometers, the thin sensing layer may provide a useful response speed to a CO2 gas and its purity variation induced temperature changes.

When the inlet gas with a temperature ($T_{GAS}$) lower than the fiber CO2 gas purity sensor temperature ($T_{FGS}$) is flushed through fiber CO2 gas purity sensor package 80, the thermal energized fiber grating structure 86 along with sensing layer 92 will dissipate thermal energy to the gas stream. In one embodiment, the thermal stabilizer's temperature may be used as a modulation parameter. For example, in one embodiment, the thermal stabilizer controlled gas chamber temperature may fall by 20-50 deg. C. when the CO2 gas stream passes through the fiber gas sensor package chamber. In yet another embodiment, the CO2 gas' heat of vaporization coefficient may be used as another modulation parameter to determine how fast the absorbed CO2 molecules in the sensing layer can be vaporized. For example, for a pure CO2 gas, the

TABLE 1

| Industrial gas | Latent heat of vaporization (kJ/kg) | Thermal conductivity (×10⁻³ W/m·K) | Heat of fusion (kJ/kg) | Cp (KJ/Mol.K) | Cv (KJ/Mol.K) | Ratio of specific heat | Specific heat capacity (kJ/kg·K) | Molecular Weight (g/mal) |
|---|---|---|---|---|---|---|---|---|
| H2S | 574 | 12.98 | 69.8 | 0.034 | — | | 1.00 | 34.08 |
| CO2 | 571 | 14.65 | 196.1 | 0.037 | 0.028 | 1.294 | 0.84 | 44.01 |
| CH4 | 510 | 32.81 | 58.7 | 0.035 | 0.027 | 1.305 | 2.18 | 16.04 |
| H2 | 454 | 168.35 | 58.2 | 0.029 | 0.021 | 1.384 | 14.38 | 2.02 |
| CO | 215 | 23.03 | 27.9 | 0.029 | 0.020 | 1.402 | 1.04 | 28.01 |
| O2 | 213 | 24.24 | 13.9 | 0.029 | 0.021 | 1.393 | 0.91 | 32.00 |
| N2 | 200 | 24.00 | 25.7 | 0.029 | 0.020 | 1.404 | 1.04 | 28.01 |
| Air | 199 | 23.94 | 22.5 | 0.029 | 0.02 | 1.403 | 1.00 | 28.95 |
| H2 | 20 | 142.64 | — | 0.020 | 0.012 | 1.664 | 5.00 | 4.00 | heat of vaporization coefficient is 571 kJ/kg, whereas for air it is 199 kJ/kg, and for N2 it is 200 kJ/kg. Thus, the purity of various blended CO2 gases can be obtained by calibrated amplitude response and time response of the fiber gas sensor signal under a constant gas flow rate.

In one embodiment, for fast response to a thermal energy transfer, sensing material 92 may comprise a nanoporous structure. The nanoporous structure allows the blended gas molecules to diffuse easily into it and also to easily diffuse out of it by transferring the thermal energy from the fiber sensor to the flowing gas and vice versa. In one embodiment, sensing material 92 is sputtered onto the fiber Bragg grating with a nanoporous morphology controlled by using low sputtering temperature of about 20-25 deg. C. In another embodiment, for fast response to a thermal energy transfer, the gas inlet and outlet are designed in lateral mode such that the gas flow stream direction is not parallel to the fiber sensor axis. When the steam direction is not parallel, a zigzag gas flow path 106 occurs and enables a direct thermal energy exchange process of the gas stream without forming a steady zero flow rate layer surrounding the fiber sensor surface.

Figure 4:
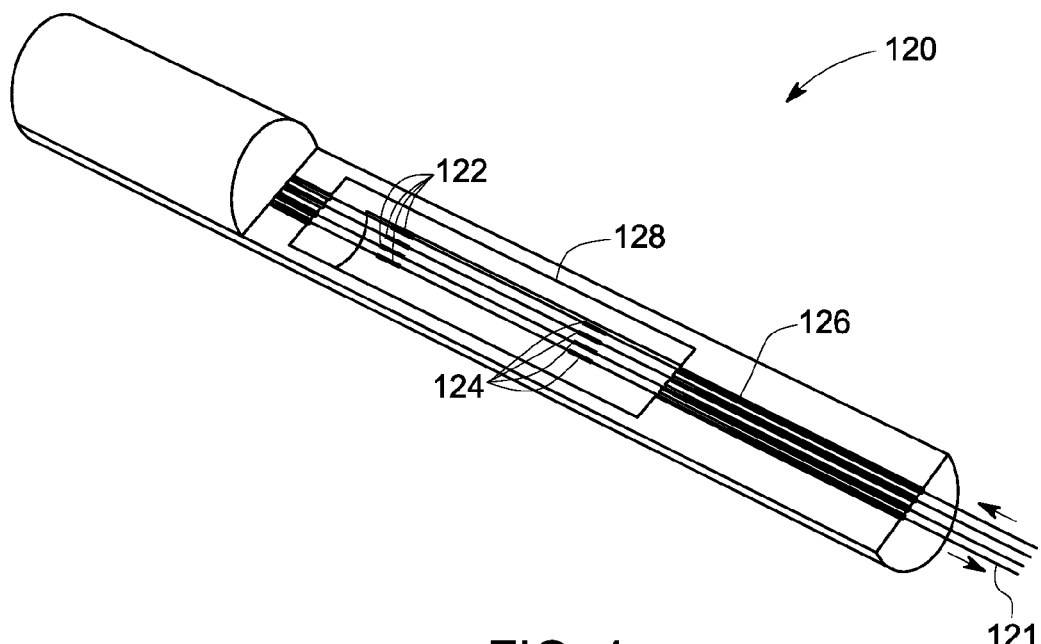
FIG. 4 is a schematic representation of a fiber CO2 gas sensing (FGS) array package for gas detection in accordance with an embodiment of the present invention.

FIG. 4 shows a fiber gas sensing (FGS) array package 120 for gas detection. In one embodiment, a gas sensor may have different sensitivity to different CO2 gases at different concentration ranges. In another embodiment, an array of the fiber gas sensors is used to determine a specious gas anomalous event. Thus, FGS array package 120 may be utilized when purity of CO2 gas in variety of blended gases is to be determined. Each FGS array may have different sensing layer materials to fit to different CO2 gas detection sensitivities. FGS array package 120 includes a plurality of fiber gas sensor arrays 121 of fiber grating structures 122 and apodized fiber grating structures 124. In the embodiment shown in the FIG. 4, four arrays of fiber grating structures are utilized. Each array is disposed within a V groove 126 of a fiber cladding 128 and is integrated with a thermally conductive sensing layer (not shown) such as layer 92 of FIG. 3. The sensing layer for each of the arrays may be functionalized with different sensing materials for sensing CO2 purity in a specific gas concentration range or with the same material when it is necessary to determine a specific CO2 gas composition and concentration. For example, one of the arrays may be optimized for sensing CO2 purity in a blended gas with a mixture of air and low-CO2 concentration, and another array may be optimized for sensing CO2 purity in a blended air gas with high-CO2 concentration. In one embodiment, all the sensors in the array are used to determine if the air concentration is lower than 5% in CO2 gas mixture, which is an important air concentration in CO2 for a hydrogen-cooled generator maintenance processes.

Figure 5:
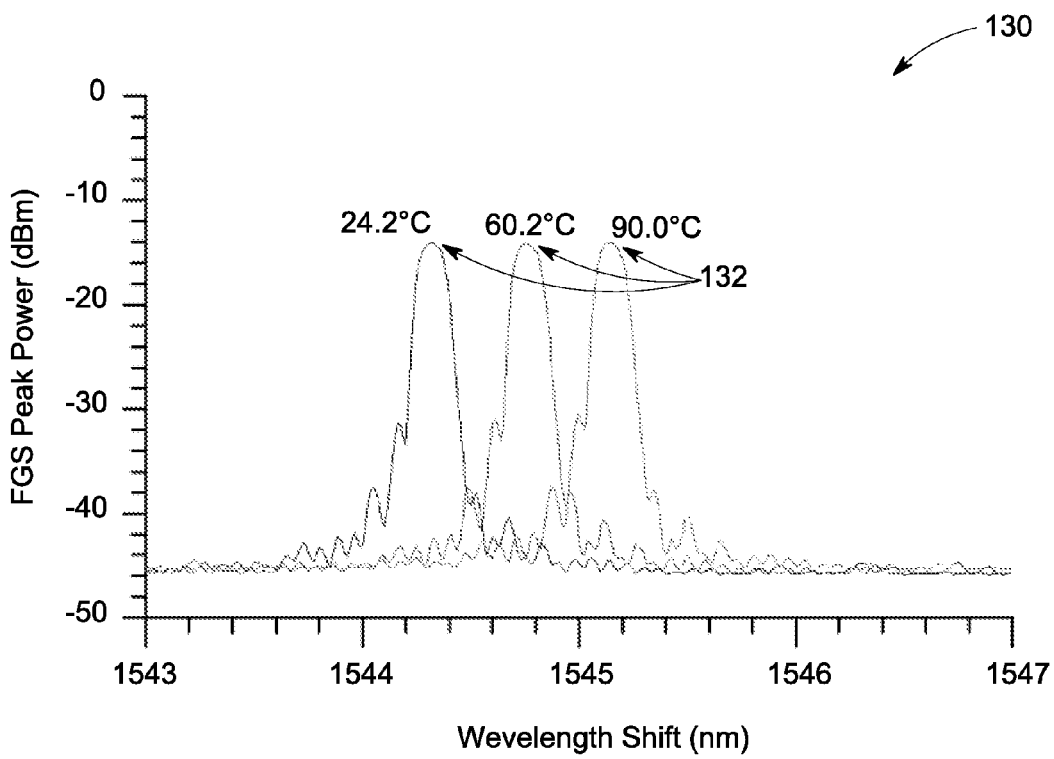
FIG. 5 is a graphical representation of a FGS wavelength shift as a function of temperature in accordance with an embodiment of the present invention.

FIG. 5 shows a plot 130 of a FGS wavelength shift as a function of temperature in accordance with an embodiment of the present invention. Plot 130 is for a fiber gas sensor functionalized with a sensing layer of a nanoporous copper (Cu) material and with a thickness of 500 nm. It can be seen from plot 130 that as a thermal sensor, the central peak power measured in decibel milliwatt (dBm) shows upshift as temperature increases from ambient to 90 deg. C. From plot 130, it can be seen that FGS peak position 132 varies with temperature and thus has dependence upon temperature. This dependence is then translated into reflectance of the optical signal and is utilized to measure purity of CO2 in a blended gas.

Figure 6:
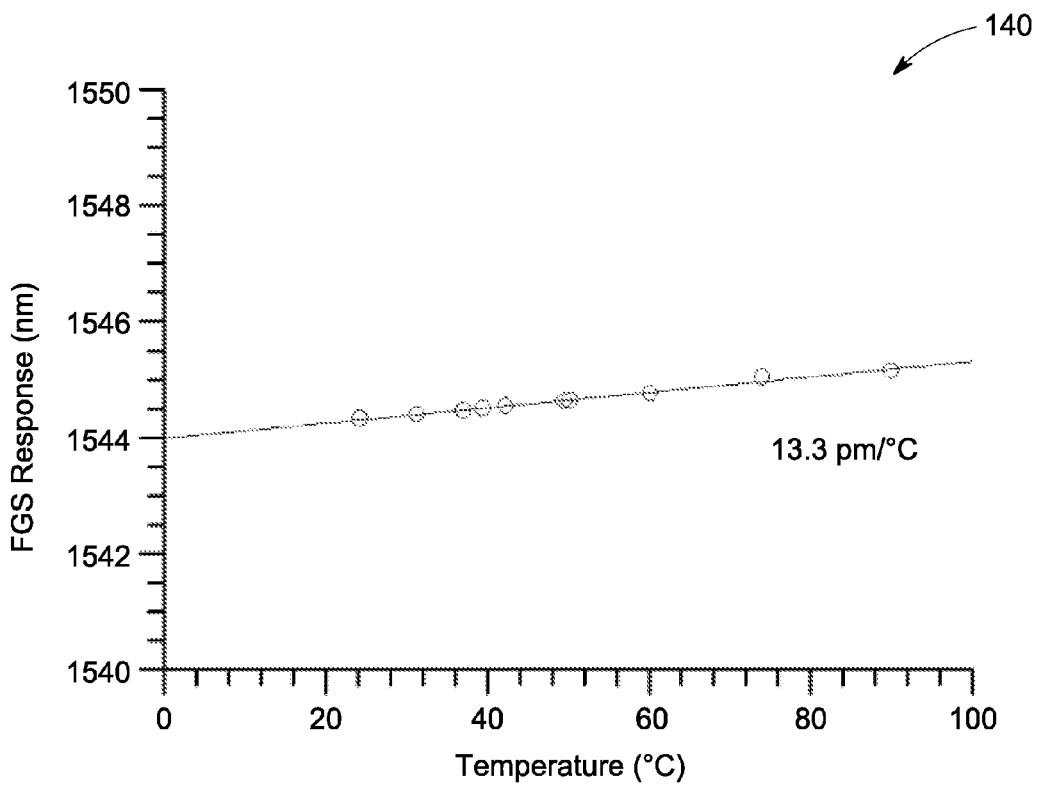
FIG. 6 is a graphical representation of a variation of wavelength shift in accordance with an embodiment of the present invention.

FIG. 6 represents a plot 140 of a variation of wavelength shift in nanometer (nm) with respect to temperature in ° C. From plot 140, it can be seen that a linear relationship exists between the fiber gas sensor wavelength shift and the external temperature with a sensitivity of 13.3 pm/° C. which is around 15.6% higher than a bared FBG temperature sensitivity (not shown) of 11.5 pm/° C. For various sensing materials with the sensing layer thickness less than 500 nanometers, the sensitivity is about (13.5±0.3) pm/° C.

Figure 7:
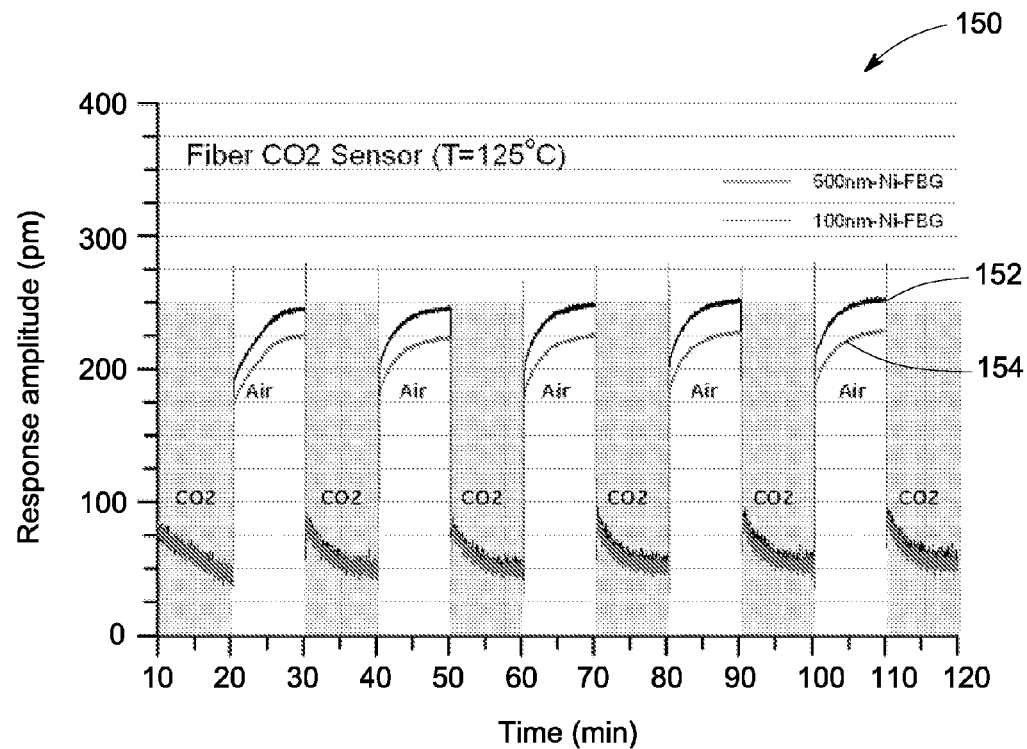
FIG. 7 is a graphical representation of two fiber CO2 gas purity sensor responses for alternating air and CO2 gas cycle measurements.

FIG. 7 shows a plot 150 of a fiber CO2 gas sensor response for CO2 purity measurement. Plot 150 includes two responses. Response 152 is for a fiber CO2 gas sensor with 500 nm nickel as the sensing layer, and another response 154 is for a fiber CO2 gas sensor with 100 nm nickel as the sensing layer. The apparatus for which CO2 purity was measured contained two gases alternatively, i) CO2 and ii) air with gas chamber temperature at 125° C. The peak wavelength of the fiber gas sensor increases or decreases with CO2 and air cycles. Thus, the response of the sensor with the thicker sensing layer (500 nm) is from 50 pm to 250 pm, whereas the response of the sensor with the thinner sensing layer (100 nm) is from 50 to 225 pm form CO2 to air gas flow. Further it can also be seen that the response time from both sensors is nearly the same.

Figure 8:
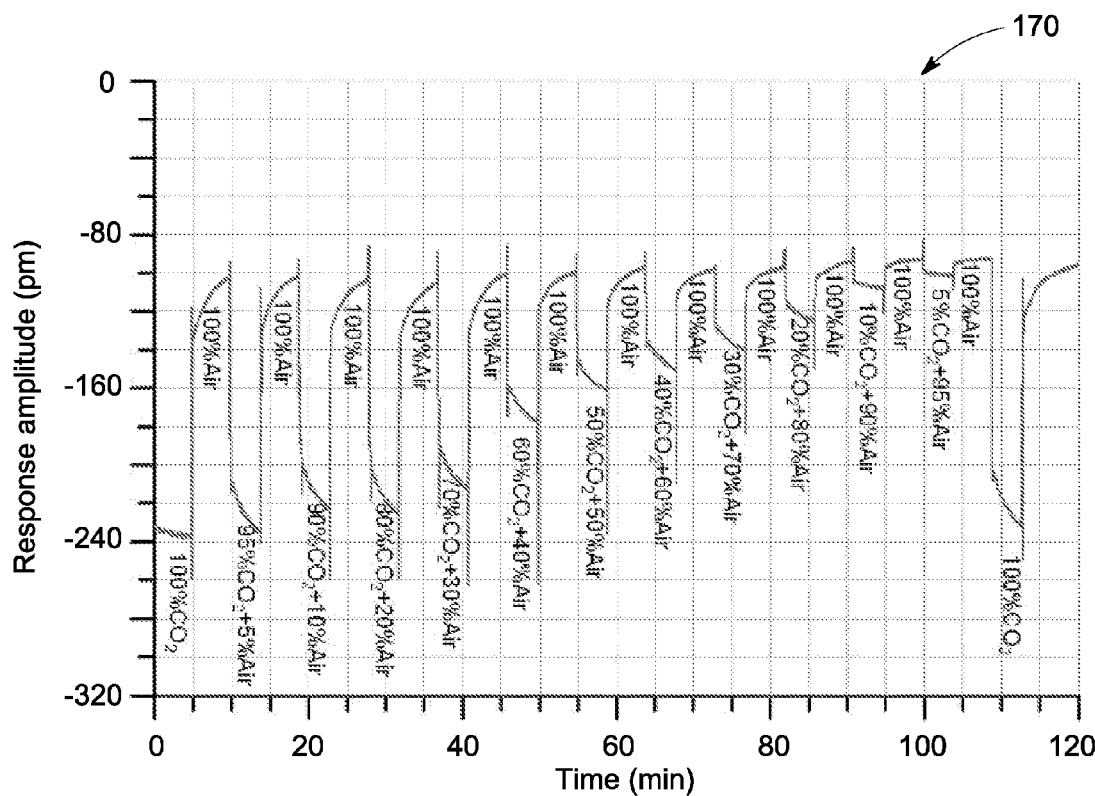
FIG. 8 is a graphical representation of fiber CO2 gas purity sensor responses to an air blended CO2 gas in accordance with an embodiment of the present invention.

FIG. 8 shows another plot 170 of a fiber CO2 gas purity sensor response for a full range of air blended CO2 gas measurements. This fiber gas purity sensor has a nickel material based sensing layer of 500 nm. The apparatus for which air blended CO2 gas is measured started from 100% CO2 to 100% air, then the CO2 purity was reduced from 95% to 5% as shown. The plot clearly demonstrates fiber CO2 gas sensor sensitivity to CO2 with 100% Air cycle used in between to differentiate the CO2 purity. For diluting CO2, dried air was introduced in the apparatus. As can be seen from the plot, the peak wavelength of the output light signal of the fiber gas sensor increases or decreases with increased or decreased CO2 purity. In one embodiment, fiber gas sensor prototypes have at least 5% sensitivity or detectability to CO2 purity change.

Figure 9:
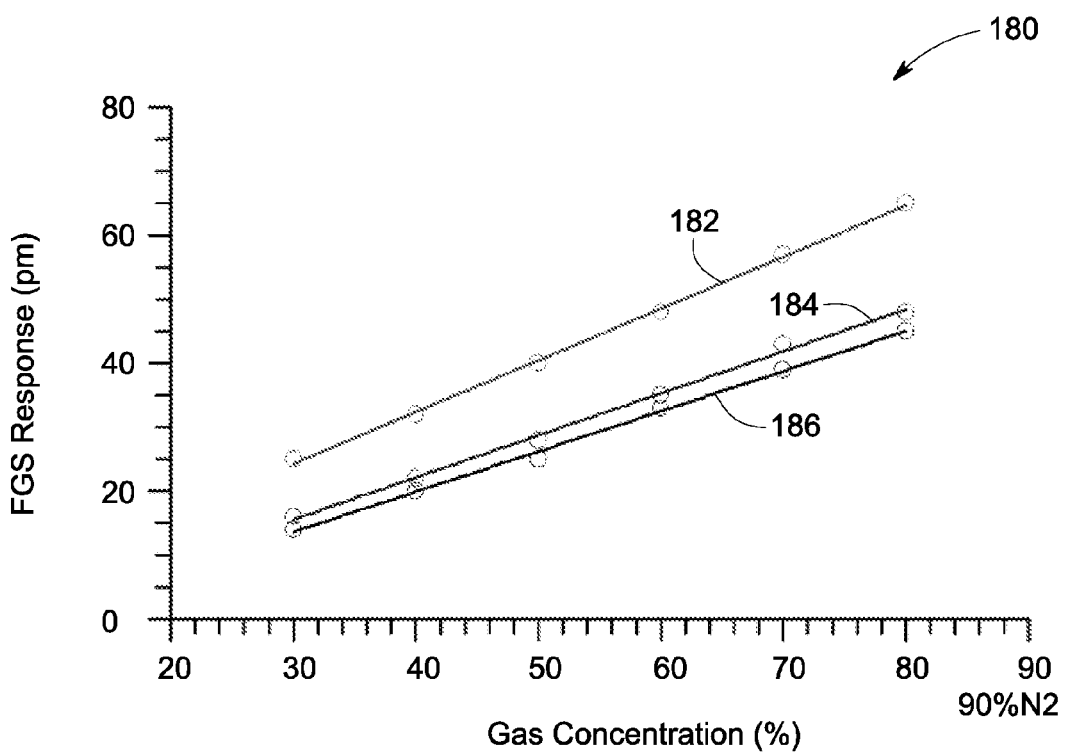
FIG. 9 is a graphical representation of a CO2 gas detection sensitivity from three fiber CO2 gas purity sensors with N2 blended CO2 gas in accordance with an embodiment of the present invention.

FIG. 9 shows a plot 180 of CO2 gas detection sensitivity from three fiber CO2 gas purity sensors with N2 blended CO2 gas. Plot 180 includes three responses. Response 182 is for a fiber CO2 gas sensor with 500 nm nickel as the sensing layer, response 184 is for a fiber CO2 gas sensor with 500 nm aluminum as the sensing layer, and another response 186 is for a fiber CO2 gas sensor with 500 nm copper as the sensing layer. It can be seen from plot 180, that for a 500 nm-thick sensing layer, aluminum, copper, and nickel coated fiber gas sensors have a sensitivity of (0.75±0.08) pm/percent for N2 blended CO2 gas when the gas package is maintained at 125 Deg. C. Since the air is similar to N2 in composition, 0.7 pm per 1% CO2 represents a typical sensitivity. However, in one embodiment, the sensitivity can be enhanced by rising thermal stabilizer's temperature or by widening the temperature difference between the sensor package and inlet gas temperature. In another embodiment, the sensitivity may be enhanced by the increasing gas flow rate. In these embodiments, the CO2 purity sensor sensitivity may be 1.5-2 times higher than in embodiments where such techniques are not employed.

Figure 10:
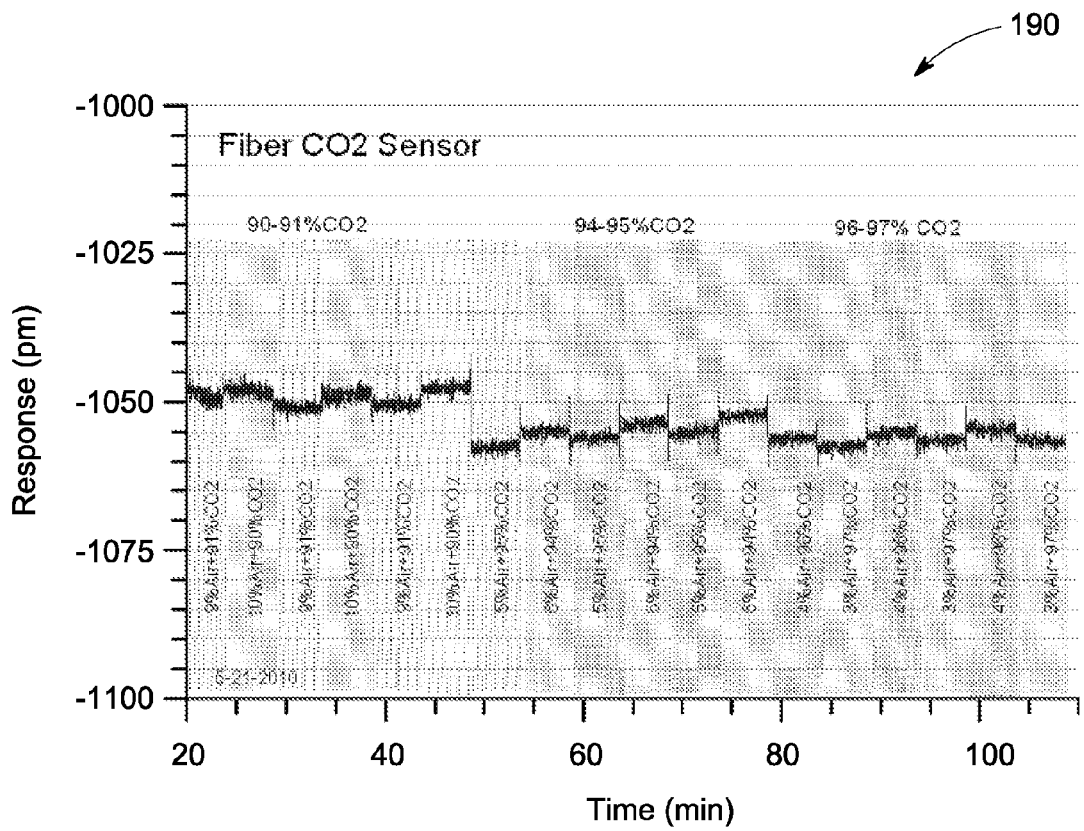
FIG. 10 is a graphical representation of fiber gas purity sensor CO2 detectability in accordance with an embodiment of the present invention.

FIG. 10 shows another plot 190 of a fiber CO2 gas purity sensor response for CO2 purity measurement. Plot 190 includes three ranges of CO2 purity detection by a fiber gas purity sensor. The apparatus for which CO2 purity is measured contained 90% CO2 at first, then the CO2 purity was increased from 90% to 97% as shown. For diluting CO2, dried air was introduced in the apparatus to produce the mixed gas, and then the mixed gas was fed into the gas sensor package. The heat energy exchange between the fiber gas sensor and diluted CO2 gas changes the wavelength shift of the fiber gas sensor because of different specific heat capacity and latent heat of vaporization coefficient variation. The peak wavelength shift of the fiber gas sensor increases or decreases with varied CO2 purity. It can be seen from the responses that the fiber gas sensor prototypes have at least 1% sensitivity or detectability to CO2 purity change. It should be noted that the gas sensor response amplitude and time may be enhanced by increasing the gas flow rate.

Figure 11:
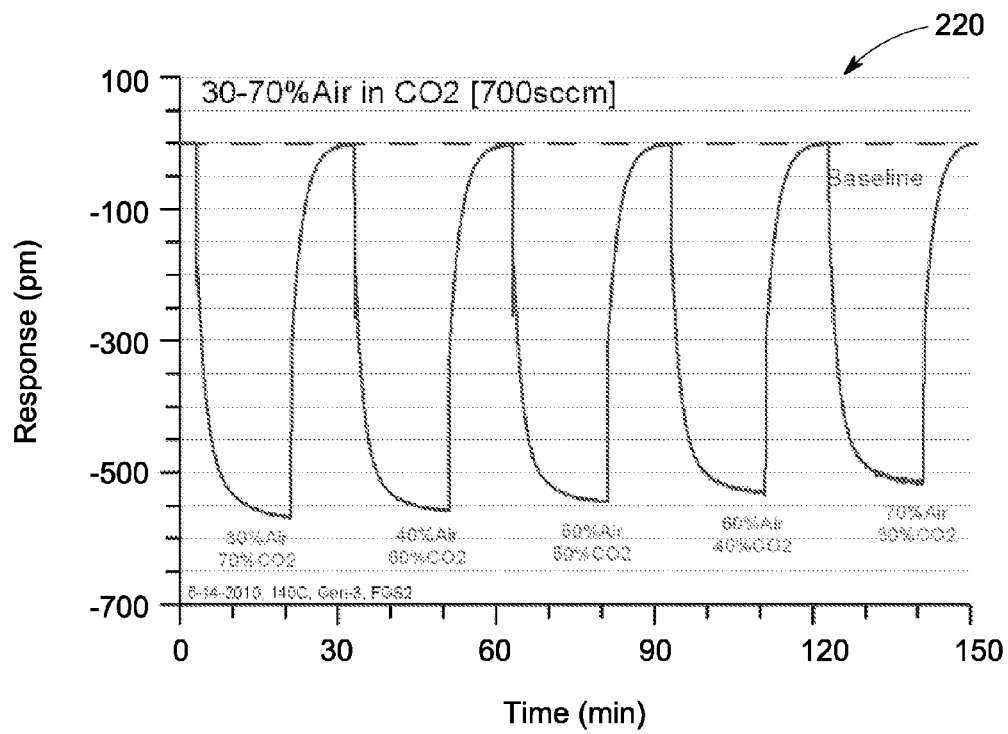
FIG. 11 is a graphical representation of a fiber CO2 gas purity sensor response with CO2 gas concentration ranging from 30% to 70% with air as a blended gas.

FIG. 11 shows yet another plot 220 of the fiber gas sensor response for CO2 purity measurement. Plot 220 demonstrates capability of the fiber gas sensor in measuring a broad range of CO2 concentrations from 30% to 70%, blended with air. The baseline 222 represents no gas flow through the gas sensor chamber, so that fiber gas sensor is at higher wavelength, determined by the thermal stabilizer temperature. Plot 220 also shows that different CO2 gas concentrations lead to different wavelength down shifts. The difference between the baseline and maximum wavelength down shift can then be used to calibrate the CO2 gas purity sensor.

Figure 12:
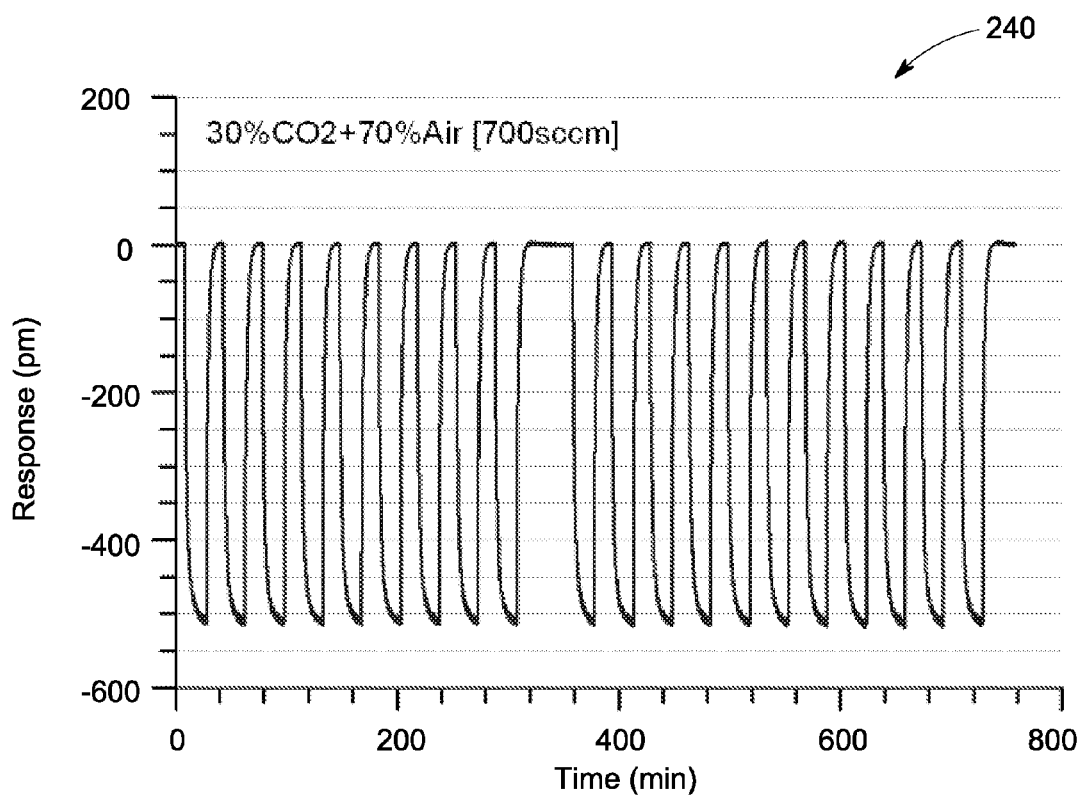
FIG. 12 is a graphical representation of repeatability of a fiber CO2 gas sensor response in the air blended CO2 gas.

FIG. 12 shows the repeatability or the long-term stability of a fiber CO2 gas sensor response 240 in an air blended CO2 gas. The testing gas is 30% CO2 blended with air. The gas sensor is cycled for 760 minutes with about 50 minutes of gas shutdown from 310-360 minutes. Since the CO2 concentration is a constant, the maximum wavelength downshift remains within 0.5% error range.

Figure 13:
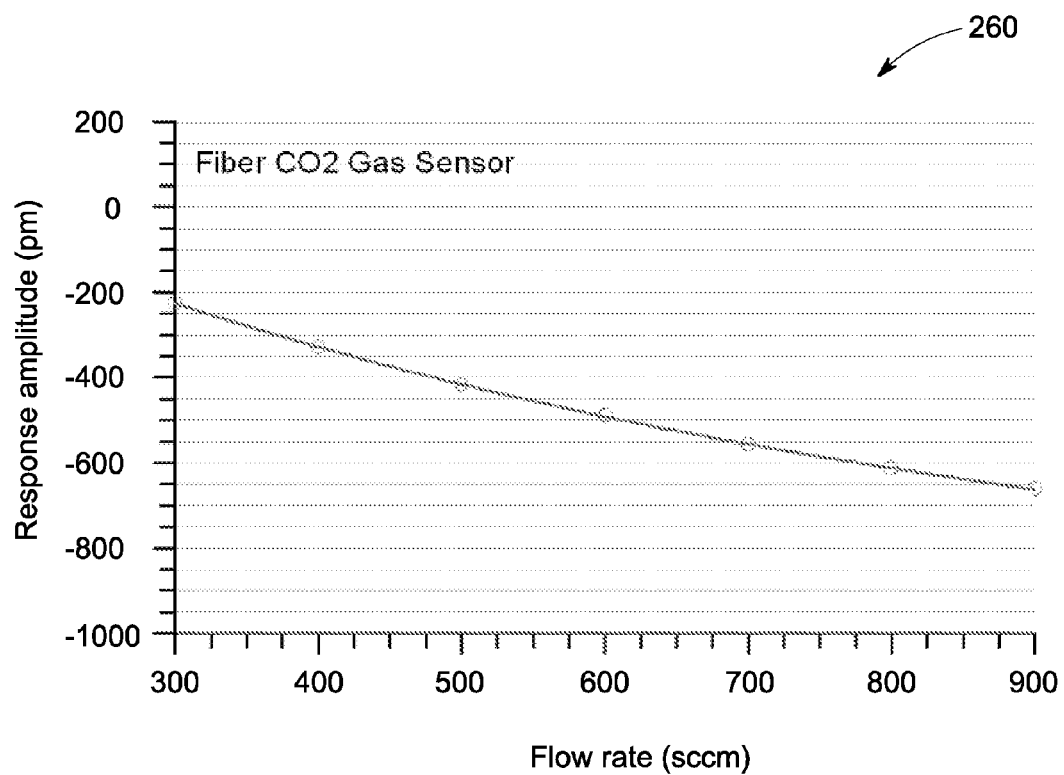
FIG. 13 is a graphical representation of fiber CO2 gas purity sensor amplitude response as a function of a gas flow rate.

FIG. 13 shows a fiber CO2 gas sensor amplitude response 260 as a function of a gas flow rate. The gas flow rate is varied from 300 sccm to 900 sccm and the variation in amplitude is observed from about 224 pm to about 650 pm. Thus, it can be seen from plot 260 that the wavelength downshift or the response amplitude and response time depends upon the gas flow rate. Under a constant flow rate, the wavelength response of a fiber gas sensor can be calibrated with CO2 purity or with blended CO2 gas.

Thus, single-point and multi-point CO2 purity detection systems have been established to calibrate wavelength shifts of one or more fiber gas sensors as a function of CO2 gas concentration. One of the advantages of the described CO2 purity sensors is high sensitivity or detectability. The sensor is capable of measuring CO2 purity in the range of 0% to 100%, has a low complexity, and can be safely deployed in harsh environments. Thus, safety measures for the apparatus where these sensors are installed may become less complex and less costly.

While only certain features of the invention have been illustrated and described herein, many modifications and changes will occur to those skilled in the art. It is, therefore, to be understood that the appended claims are intended to cover all such modifications and changes as fall within the true spirit of the invention.

The invention claimed is:

1. A carbon dioxide (CO2) purity sensor package, comprising:
    a fiber core;
    a fiber cladding;
    a periodic refractive index modulated fiber grating structure within the fiber core;
    a thermally conductive sensing layer positioned about a portion of the fiber cladding surrounding the periodic refractive index modulated fiber grating structure, wherein the thermally conductive sensing layer comprises a nanostructural thin film; and
    a gas chamber enclosing the fiber cladding with the thermally conductive sensing layer.

2. The CO2 purity sensor package of claim 1 further comprising an apodized fiber grating for sensing a baseline temperature and variations in the baseline temperature.

3. The CO2 purity sensor package of claim 1, wherein the periodic refractive index modulated fiber grating structure comprises one of a blazed profile, an apodized profile, or a blazed and apodized profile.

4. The CO2 purity sensor package of claim 1, wherein the fiber core comprises germanium dioxide (GeO2) or fluorine (F) co-doped silica.

5. The CO2 purity sensor package of claim 4, wherein the fiber cladding comprises pure silica or fluorine doped silica.

6. The CO2 purity sensor package of claim 1, wherein the gas chamber is hermetically sealed and comprises a fiberglass protected thermal stabilizer for shielding the sensor package from ambient temperature variation and keeping the sensor package in an isotheiinal status.

7. The CO2 purity sensor package of claim 6, wherein the thermal stabilizer comprises a heating tape, a heating pad, or a heating wire.

8. The CO2 purity sensor package of claim 1, wherein a thermal conductivity of the thermally conductive material ranges from about 71 W/m.K to about 429 W/m.K.

9. The CO2 purity sensor package of claim 8, wherein the thermally conductive material comprises aluminum, copper, nickel, cobalt, silver, gold, palladium or platinum.

10. The CO2 purity sensor package of claim 8, wherein the thermally conductive material comprises diamond, diamond-like-carbon, or Indium tin oxides with controlled porous structure or nanoparticle morphology.

11. The CO2 purity sensor package of claim 1, wherein the thickness of the thermally conductive sensing layer ranges from tens of nanometers to hundreds of nanometers.

12. The CO2 purity sensor package of claim 1, wherein the thermally conductive sensing layer comprises a sandwiched triple layer structure comprising a first layer of a titanium or a chrome based bonding material, a middle layer of the thermally conductive material, and a bottom layer comprising a capping layer for protecting the thermally conductive material against oxidization, corrosion, and erosion.

13. The CO2 purity sensor package of claim 1, wherein the periodic refractive index modulated fiber grating structure comprises a plurality of fiber Bragg grating structures and the thermally conductive sensing layer comprises a plurality of thermally conductive sensing layers positioned with respect to respective periodic refractive index modulated fiber Bragg grating structures, wherein at least some of the thermally conductive sensing layers are functionalized for measuring CO2 purity in different types of blended gases.

14. The CO2 purity sensor package of claim 1, further comprising a valve for controlling a flow of a blended gas, and a lateral gas inlet and a lateral gas outlet for inducing zigzag gas flow path.

15. The CO2 purity sensor package of claim 14, further comprising a flow meter for measuring the flow of the blended gas.

* * * * *